United States Patent [19]

Johns

[11] Patent Number: 4,872,869
[45] Date of Patent: Oct. 10, 1989

[54] LOW PROFILE OSTOMY DEVICE

[75] Inventor: Owen L. Johns, Madeira Beach, Fla.

[73] Assignee: Smith & Nephew (Latin America), Inc., Largo, Fla.

[21] Appl. No.: 210,910

[22] Filed: Jun. 24, 1988

Related U.S. Application Data

[63] Continuation of Ser. No. 872,305, Jun. 9, 1982, abandoned.

[51] Int. Cl.$^4$ .............................................. A61F 5/44
[52] U.S. Cl. .................................... 604/342; 604/339
[58] Field of Search ...................... 604/277, 327–345; 128/767; 285/331, DIG. 22; 383/63–66; 150/55; 220/306, 307

[56] References Cited

U.S. PATENT DOCUMENTS

| | | | |
|---|---|---|---|
| 2,798,631 | 7/1957 | Engel | 220/306 |
| 3,416,199 | 12/1968 | Imamura | 383/63 |
| 3,528,420 | 9/1970 | Nielsen | 604/342 |
| 3,588,149 | 6/1971 | Demler et al. | 285/331 |
| 4,026,581 | 5/1977 | Pasbrig | 285/331 |
| 4,460,363 | 7/1984 | Steer et al. | 604/342 |
| 4,468,227 | 8/1984 | Jensen | 604/327 |
| 4,610,677 | 9/1986 | Mohiuddin | 604/339 |

FOREIGN PATENT DOCUMENTS

| | | | |
|---|---|---|---|
| 0098718 | 1/1984 | European Pat. Off. | 604/342 |
| 2163350 | 2/1986 | United Kingdom | 604/338 |

Primary Examiner—C. Fred Rosenbaum
Assistant Examiner—Mario Costantino
Attorney, Agent, or Firm—Jacobs & Jacobs

[57] ABSTRACT

A low profile ostomy device includes an ostomy bag with an opening, a first coupling member attached to the ostomy bag at the opening, and a second coupling member for attachment to a user's body. The first and second coupling members are engaged by the joining of an engaging element on each of the members, the engagement providing a tight mechanical seal between the members within the ostomy bag.

9 Claims, 2 Drawing Sheets

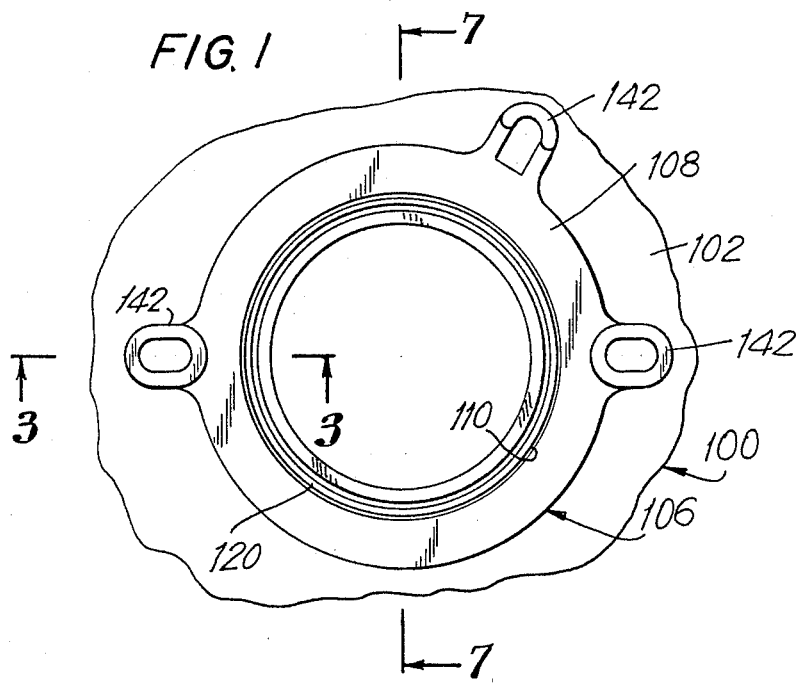
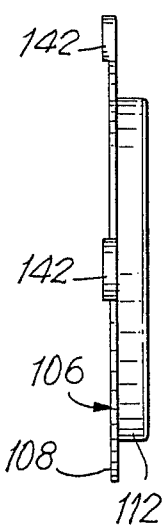
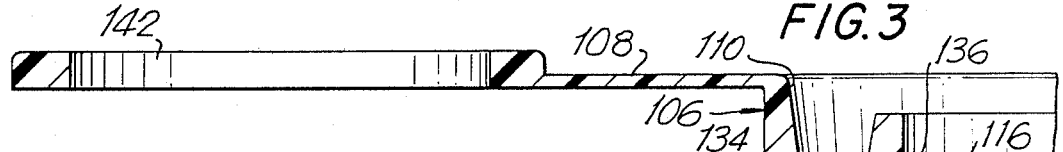
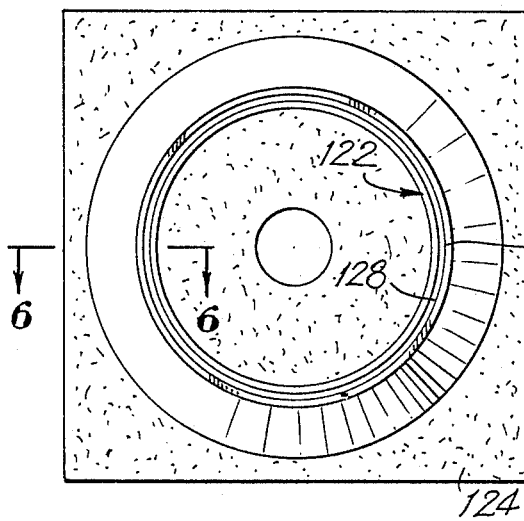
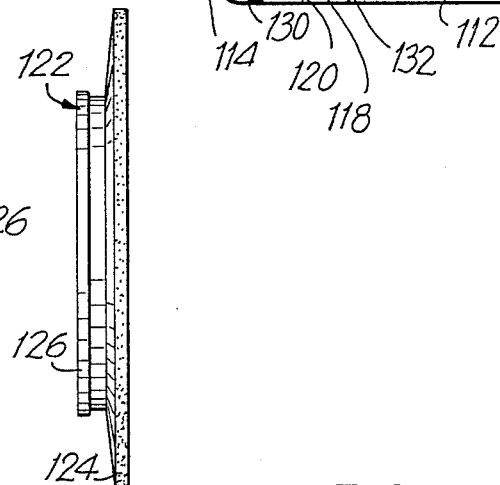
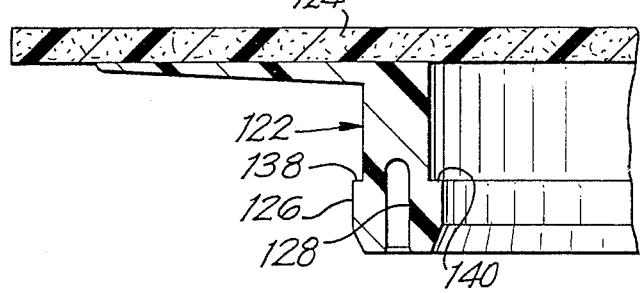

LOW PROFILE OSTOMY DEVICE

This is a continuation of application Ser. No. 872,305, filed on June 9, 1986 now abandoned.

BACKGROUND OF THE INVENTION

This invention concerns an improved means for securing an ostomy bag to a user.

Ostomy bags are normally secured to a user's body through a coupling which releasably connects the bag to a pad or dressing adhesively attached to the body. This coupling should allow ready entrance of a stoma into the bag, provide a tight mechanical seal to prevent leakage, and be readily released to assure convenient replacement of the bag. In addition, the bag should be comfortable to the user.

Early ostomy devices, such as that disclosed in West German Auslegeschrift No. 1105558, provided suitable mechanical seal but lacked means for convenient replacement of the bag. Other ostomy couplings, such as that disclosed in U.S. Pat. No. 4,460,363, by the nature of their construction fail to allow the ostomy bag to fit comfortably close to the user's body.

It is, therefore, the primary objective of the present invention to provide an ostomy device which assures ready access for the stoma, tight mechanical seal and convenient replacement of the bag, and also allows for a closer fit of the bag to the body.

SUMMARY OF THE INVENTION

The desired objective is accomplished with a low profile ostomy device, which comprises:

(a) an ostomy bag provided with a stoma-encircling opening;

(b) a first coupling member comprising a flat ring portion attached to the ostomy bag with an aperture substantially of the same size as and coincident with the ostomy bag opening, and a first engaging element depending from the ring portion substantially at the aperture and extending into the ostomy bag; and (c) a second coupling member comprising means for attachment to a user's body, and a second engaging element for engagement with the first engaging element and having an aperture substantially of the same size as the ostomy bag opening, the engagement providing a mechanical seal between the first and second coupling members within the ostomy bag.

In a preferred embodiment, the first engaging element is in the form of a channel with two sides and a bottom, and the second engaging element is in the form of a flange. The channel bottom may comprise a rib adapted to engage a groove in the flange which splits the flange into two parts. In such case, the flange is preferably formed of a flexible, resilient material and the rib in the first engaging element is slightly wider than the groove in the second engaging element to thereby force the split flange of the second engaging element against the channel sides of the first engaging element when the first and second engaging elements are engaged.

To further improve the mechanical seal, the channel of the first engaging element may have an inner wall with at least one protrusion on the wall, and the split flange has at least one protrusion which interlocks with the wall protrusion when the first and second engaging elements are engaged.

With the present ostomy device, the first coupling member is conveniently heat sealed to the ostomy bag; the ring portion and the first engaging element of the first coupling member may be integral; the ring portion of the first coupling member may comprise at least one radially extending tab adapted to be gripped by the user; and the attaching means of the second coupling member preferably comprises a layer of adhesive. The first and second coupling members of the ostomy device are readily formed of polyethylene.

BRIEF DESCRIPTION OF THE DRAWINGS

The novel features and advantages of the present invention will become apparent from a reading of the following detailed description in conjunction with the accompanying drawings wherein:

FIG. 1 is an elevational view of the first coupling member and a portion of the attached ostomy bag of a preferred embodiment of the present ostomy device, looking in a direction outwardly from the user;

FIG. 2 is a side elevational view of the first coupling member shown in FIG. 1;

FIG. 3 is an enlarged cross-sectional view of the first coupling member only taken along the line 3—3 of FIG. 1;

FIG. 4 is an elevational view of the second coupling member of the present ostomy device, looking in a direction toward the user;

FIG. 5 is a side elevational view of the second coupling member shown in FIG. 4;

FIG. 6 is an enlarged cross-sectional view taken along the line 6—6 of FIG. 4;

DETAILED DESCRIPTION OF THE INVENTION

A preferred embodiment of the low profile ostomy device of the present invention is shown in FIGS. 1–8.

This device 100 comprises an ostomy bag 102 having an opening 104 of a size suitable for encircling a user's stoma (not shown). The ostomy bag 102 may be of various sizes and shapes and constructed of various materials, as is well known in the art. Normally, ostomy bag 102 will be constructed from plastic sheet such as polyethylene and will be of flat design to minimize its protrusion from the user's body. Opening 104 is normally in the upper portion of ostomy bag 102, and would be available in various sizes depending on the size of the user. While opening 104 may be of any shape, it will normally be circular.

Figure 7:
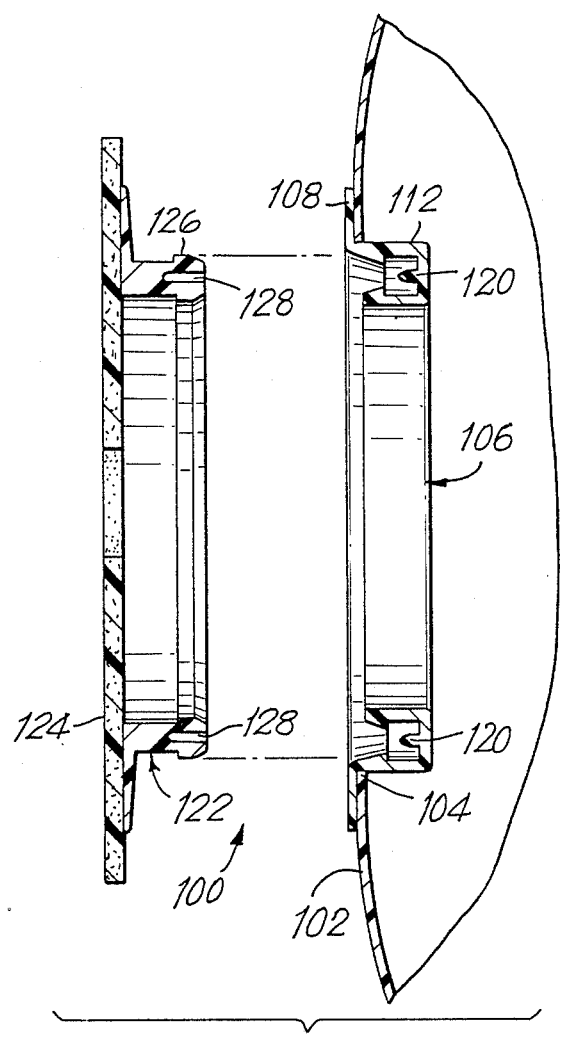
FIG. 7 is an exploded cross-sectional view of the first coupling member taken along the line 7—7 of FIG. 1 and of the second coupling member taken along the line 7—7 of FIG. 4.
Figure 8:
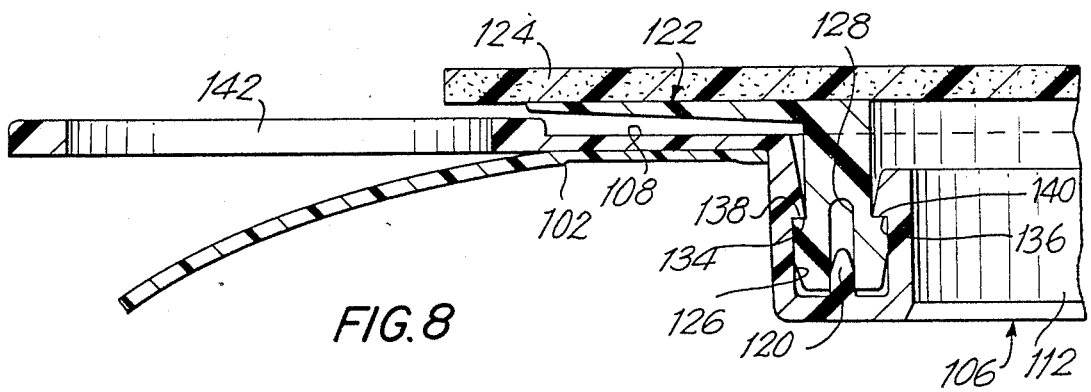
FIG. 8 is an enlarged cross-sectional view taken along the line 3—3 of FIG. 1 and line 6—6 of FIG. 2 when the first and second coupling members are fully engaged.

A first coupling member 106 shown in FIGS. 1–3 comprises a flat ring portion 108 which is attached to the ostomy bag 102 by heat sealing as shown in FIG. 8. Ring portion 108 has an aperture 110 substantially of the same size and shape as and coincident with opening 104. A first engaging element 112, which is integral with ring portion 108 as shown in FIG. 3, depends from ring portion 108 at aperture, 110 into ostomy bag 102. Engaging element 112 is in the form of a channel with a long side 114, a short side 116 and a bottom 118. A rib 120 on channel bottom 118 extends into channel 112 substantially parallel to and equidistant from channel sides 114,116.

A second coupling member 122 shown in FIGS. 4–6 comprises an adhesive layer 124 for attaching second coupling member 122 to a user's body (not shown) and a second engaging element 126 for engagement with first engaging element 112 within ostomy bag 102 as shown in FIG. 8, the engagement providing a mechanical seal between first coupling member 106 and second coupling member 122. Second engaging element 126 is in the form of a flange formed from a flexible, resilient material such as polyethylene and split into two essentially equal parts by groove 128.

Since rib 120 in channel 112 is slightly wider than groove 128, when channel 112 and flange 126 are engaged, the split portions of flange 126 are forced by rib 120 against channel sides 114,116, thereby providing an improved mechanical seal between first and second coupling members 106,122. To further enhance the sealing action, channel 112 has on each of inner walls 130,132 a protrusion 134,136 on the portion of wall 130,132 opposite channel bottom 118, and flange 126 has on the outside end of each of the split portions a similar protrusion 138,140. Upon engaging flange 126 with channel 112, flange protrusions 138,140 slide over and snap behind channel protrusions 134,136 to thereby provide a friction fit between flange 126 and channel 112 as shown on FIG. 8.

As shown on FIG. 1, first coupling member 106 may include one or more radially extending tabs 142 as part of ring portion 108 for gripping by the user. Such tab 142 is common in the art.

While other materials may be used, polyethylene is the material of choice for both first coupling member 106 and second coupling member 122.

The present ostomy device, by having the coupling means for securing the ostomy bag to a user within the bag itself, allows an ostomy bag to fit closer to the user and provides the advantage, among others, of a marked improvement in the overall aesthetics of the device.

I claim:

1. A low profile ostomy device which comprises:
   (a) an ostomy bag provided with a stoma-encircling opening through the side thereof;
   (b) a first coupling member comprising a flat ring portion attached to the ostomy bag through the opening and having an aperture substantially of the same size as and coincident with the ostomy bag opening, said ring having a first engaging element in the form of an annular channel having two sides and a bottom, the bottom of the channel having a rib extending upward within the channel; said first engaging means extending into the ostomy bag; and
   (c) a second coupling member comprising means for attachment to a user,s body, said second member having a second engaging element for engagement with the first engaging element, said second member having an aperture of substantially the same size as the ostomy bag opening, said second engaging element comprising an annular flange having a central groove therein which mates with said rib to provide a seal between the first and second engaging means.

2. The ostomy device according to claim 1 wherein the flange is formed of a flexible, resilient material and the rib is slightly wider than the groove in the second engaging element to thereby force the flange of the second engaging element against the channel sides of the first engaging element when the first and second engaging elements are engaged.

3. The ostomy device according to claim 2 wherein the channel has an inner wall with at least one protrusion therefrom, and the flange has at least one protrusion which interlocks with the wall protrusion when the first and second engaging elements are engaged.

4. The ostomy device according to claim 1 wherein the first coupling member is heat sealed to the ostomy bag.

5. The ostomy device according to claim 1 wherein the ring portion and the first engaging element of the first coupling member are integral.

6. The ostomy device according to claim 1 wherein the ring portion of the first coupling member comprises at least one radially extending tab adapted to be gripped by the user.

7. The ostomy device according to claim 1 wherein the attaching means of the second coupling member comprises an adhesive.

8. The ostomy device according to claim 1 wherein the first and second coupling members are each polyethylene.

9. The ostomy device according to claim 7 wherein the second coupling member comprises a flat ring having said flange integral therewith secured to a suitable material which on the body adhering portion thereof has a layer of adhesive.

* * * * *